United States Patent [19]

Brouard et al.

[11] 4,008,213
[45] Feb. 15, 1977

[54] AZO DYESTUFFS CONTAINING A CINNAMONITRILE RESIDUE

[75] Inventors: Claude Marie Henri Emile Brouard, Sotteville-les-Rouen; Jean Marie Louis Leroy, St. Etienne du Rouvray; Jean-Pierre Henri Stiot, Saint Pierre les Elbeuf, all of France

[73] Assignee: Ugine Kuhlmann, Paris, France

[22] Filed: Mar. 11, 1971

[21] Appl. No.: 123,414

[30] Foreign Application Priority Data

Mar. 12, 1970 France .............................. 7008829

[52] U.S. Cl. ........................ 260/160; 106/308 Q; 208/12; 260/37 R; 260/38; 260/39 P; 260/40 R; 260/42.21; 260/152; 260/154; 260/155; 260/159; 260/162; 260/163; 260/176; 260/184; 260/193; 260/197; 260/205; 260/206; 260/207; 260/207.1; 260/207.5; 260/465 E; 260/465 G; 260/465 K

[51] Int. Cl.² .................. C09B 29/08; C09B 29/10; C09B 29/26; C09B 29/28

[58] Field of Search .......... 260/162, 152, 163, 160, 260/159, 154, 206, 205, 155, 165, 193, 197, 198, 200, 207, 207.1, 207.5, 199, 164

[56] References Cited
UNITED STATES PATENTS

| | | | |
|---|---|---|---|
| 3,090,780 | 5/1963 | Gaetani | 260/186 |
| 3,222,355 | 12/1965 | Gaetani | 260/186 |
| 3,578,654 | 5/1971 | Favre | 260/186 |

Primary Examiner—Floyd D. Higel
Attorney, Agent, or Firm—Beveridge, Degrandi, Kline & Lunsford

[57] ABSTRACT

Dyestuffs of the general formula:

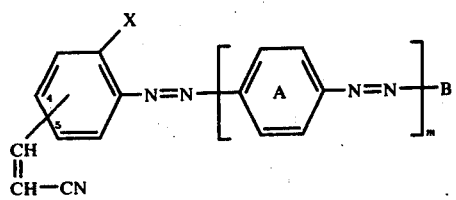

in which the radical —CH=CH—CN is fixed in the 4- or 5- position, X represents a hydrogen or chlorine atom, the benzene nucleus A is unsubstituted or substituted by at least one chlorine atom or alkyl, alkoxy or acylamino group, $m$ is the number 0 or 1, and B represents the residue of a coupling compound containing no sulphonic or carboxylic acid group.

The dyestuffs in which $m$ represents zero may be prepared by diazotizing a base of the formula:

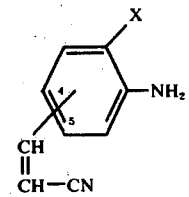

and coupling the diazo derivative with a coupling compound BH wherein X and B have the same significance as set out above.

The dyestuffs in which $m$ is equal to 1 may be prepared by coupling the diazo derivative of a base of the formula:

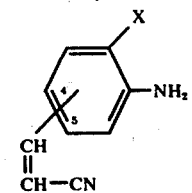

with an amine of the formula:

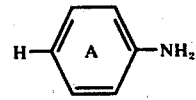

diazotizing the amino-monoazo dyestuff thus obtained and coupling with a coupling compound BH wherein

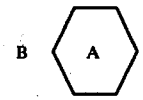

have the same significance as set out above.

The dyestuffs may be used for the coloration of synthetic fibers such as fibers based on cellulose diacetate, cellulose triacetate and, more particularly aromatic polyesters and polyamides.

3-amino-cinnamonitrile or 3-amino-4-chloro-cinnamonitrile or 4-amino-3-chloro-cinnamonitrile. These may be prepared by Meerwein's reaction between acrylonitrile and a diazonium chloride of m- or p-nitraniline, dehydrohalogenation by means of an alkali and then reduction of the nitro group.

3 Claims, No Drawings

AZO DYESTUFFS CONTAINING A CINNAMONITRILE RESIDUE

The present invention relates to new water-insoluble azo dyestuffs which are of particular interest for the colouration of synthetic fibres, such as fibres based on cellulose diacetate, cellulose triacetate and, more particularly, aromatic polyesters and polyamides.

These new dyestuffs may be represented by the general formula:

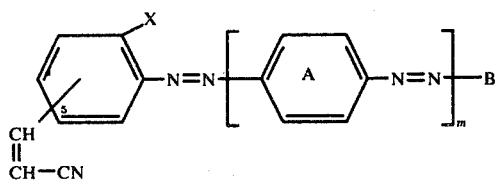

in which the radical —CH=CH—CN is fixed in the 4- or 5-position X represents a hydrogen or chlorine atom, the benzene nucleus A may be substituted by one or more chlorine atoms or alkyl, alkoxy or acylamino groups, m is the number 0 or 1, and B represents the residue of a coupling compound, possibly substituted, but containing no sulphonic or carboxylic acid groups. The preferred alkyl and alkoxy groups are those containing 1 to 4 carbon atoms and the acyl groups may belong, for example, to the aliphatic, e.g. acetyl, aromatic, e.g. benzoyl, or araliphatic, e.g. cinnamoyl, series.

The coupling compounds of residue B may belong, to a wide variety of series, such as, for example, the benzene, naphthalene, quinoline, carbazole, diphenylene oxide, indazole, coumarin, acylacetarylide, pyrazolone, hydroxyquinoline or indole series. Specific examples of coupling compounds are:

1. the amines of the formula:

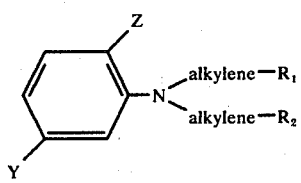

in which Y represents a hydrogen or chlorine atom or a methyl, methoxy or acylamino group, Z represents a hydrogen atom or a methyl or methoxy group, $R_1$ and $R_2$ may be the same or different and each may represent a hydrogen atom or a cyano, hydroxy, alkoxycarbonyl, acyloxy, acyl, alkylsulphonyl, carbonamido or alkoxycarbonyloxy group. The preferred alkyl, alkoxy and alkylene groups are those containing 1 to 4 carbon atoms and the acyl groups may belong, for example, to the aliphatic, e.g. acetyl, aromatic, e.g. benzoyl or araliphatic, e.g. cinnamoyl, series.

2. the pyrazolones of the formula:

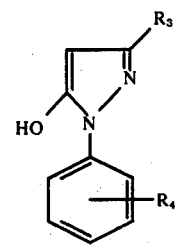

in which $R_3$ represents a hydrogen atom, a methyl or alkoxycarbonyl group or a carbonamido group which may be substituted by alkyl groups containing 1 to 4 carbon atoms and $R_4$ represents a hydrogen or chlorine atom or a cyano, nitro, methyl or sulphonamido group. The alkoxy group preferably contains 1 to 4 carbon atoms.

3. phenol and its homologs such as, for example, p-cresol and the naphthols.
4. the N-alkyl-4-hydroxy-2-quinolones,
5. the hydroxycarbazoles
6. the hydroxydiphenylene oxides, and
7. the indoles.

The dyestuffs of formula (I) in which m represents zero may be prepared, for example by diazotising a base of the general formula:

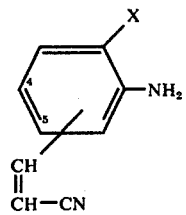

and coupling the diazo derivative with a coupling compound BH, the significance of X and B being as defined above.

The dyestuffs of formula (I) in which m is equal to 1 may be prepared, for example, by coupling the diazo derivative of a base of formula (IV) with an amine of formula:

diazotising the amino-monoazo dyestuff thus obtained, and coupling with a coupling compound B - H, the significance of B and

being as defined above.

The bases of formula (IV), with the exception of p-aminocinnamonitrile, are new products. They may be prepared, for example, by Meerwein's reaction between acrylonitrile and a diazonium chloride from m- or p-nitraniline, dehydrohalogenation by means of an alkali such as, for example, sodium acetate, and finally reduction of the nitro group.

In view of their tinctorial applications, it is advantageous for the dyestuffs obtained to be in a finely divided state. For this reason, the dyestuffs according to the invention are preferably pre-dispersed and provided in the form of a paste or powder. This form may be obtained by mixing the dyestuff in paste form with a dispersing agent, and possibly with an inert diluent. If desired the mixing may be followed by drying and grinding. The dyestuffs thus treated can then be used, for example, for dyeing in a long or short bath, in foularding or in printing. Examples of dispersing agents which may be used are the products resulting from the condensation of naphthalenesulphonic acids with formaldehyde, especially the dinaphthylmethane disulphonates, esters of sulphonated succinic acid, alkali metal salts of sulphuric esters of fatty alcohols, for example, sodium lauryl-sulphate, ligno-sulphonates, soaps, alkali metal salts of the sulphuric esters of monoglycerides of fatty acids or the products obtained by the condensation of the cresols with formaldehyde and naphthol-sulphonic acids, and the condensation products of 4,4'-dihydroxy-diphenylsulphone with formaldehyde and alkali metal bisulphites.

The dyeing of polyester fibres may be carried out, for example, in the presence of a carrier at a temperature from 80° C. to 125° C. inclusive or without a carrier under pressure at a temperature from 100° C. and 140° C. inclusive.

The fibres can also be foularded or printed with aqueous dispersions of the new dyestuffs, the impregnation obtained being then fixed at a temperature from between 140° C. to 230° C. inclusive for example by means of steam, air or by contact with a heated surface. The range of temperature from 180° C. to 200° C. inclusive is particularly favourable, since the dyestuffs diffuse rapidly into the polyester fibres and do not sublime even if the action of these high temperatures is prolonged. This enables fouling of the dyeing apparatus to be avoided.

Cellulose diacetate is preferably dyed by exhaustion at a temperature from 65° C. to 85° C. inclusive and cellulose triacetate and polyamide fibres are preferably dyed at a temperature up to 115° C. The most favourable pH region is between 2 and 9 inclusive and especially between 4 and 8 inclusive. Like the polyester fibres, the triacetate and polyamide fibres can be foularded or printed with an aqueous suspension of the new dyestuffs with subsequent fixing of the impregnations obtained at a temperature from 140° C. to 210° C. inclusive.

During foularding or printing, the usual thickeners may be used, for example, modified or unmodified natural products, such as alginates, crystalline gum, carob, gum tragacanth, carboxymethyl-cellulose, hydroxyethylcellulose, starch, or synthetic products such as polyacrylic amides or polyvinyl alcohols.

The shades thus obtained are remarkably fast to thermal fixation, sublimation, creasing, combustion gases, overdyeing, dry cleaning, chlorine and wet tests, for example water, washing and sweat. The reserve of the natural fibres, especially of wool and cotton, and the dischargeability are good. The fastness to light is remarkable even with light shades, so that the new dyestuffs are very suitable for the production of fashion shades. The dyestuffs resist boiling and reduction at temperatures from 80° C. to 220° C. inclusive. This stability is not altered by the bath ratio nor by the presence of dyeing accelerators.

Certain dyestuffs of formula (I) can be used for the bulk colouration of varnishes, oils, synthetic resins and synthetic fibres spun from their solutions in organic solvents.

The invention is illustrated by, but not limited to, the following Examples, in which the parts are parts by weight unless the contrary is indicated.

EXAMPLE 1

140 parts of p-aminocinnamonitrile are dissolved in 1000 parts of water and 220 parts by volume of 30% hydrochloric acid and are diazotised by adding 70 parts of sodium nitrite. The solution of the diazo derivative is introduced into a solution of 231 parts of 1-phenyl-3-ethoxycarbonyl-5-pyrazolone in 2000 parts of water containing 120 parts of sodium carbonate. The dyestuff obtained is filtered off and mixed with a dispersing agent. It dyes polyester fibres an orange yellow shade possessing excellent fastness to light and to sublimation and indeed to the conditions set out above.

The p-aminocinnamonitrile, used in this Example, may be prepared as follows:

A mixture of 120 parts of acrylonitrile and 1000 parts of acetone is introduced into the solution of the diazo derivative obtained from 276 parts of p-nitroaniline. Then, 40 parts of cupric chloride crystallised with 2 molecules of water are added and the mixture is stirred vigorously. The evolution of nitrogen is exothermic and the temperature should be kept at 30°–32° C. by means of a cooling bath. When the diazonium chloride has disappeared (6 hours), yellow leaflets melting at 108° C. are filtered off. After recrystallisation from methanol, one obtains 330 parts of 2-chloro-3-(4-nitrophenyl) propionitrile which melts at 112° C. This product is then dehydrohalogenated by means of 200 parts of crystallised sodium acetate in a mixture of 340 parts of water and 800 parts of ethyl alcohol. The mixture is refluxed for 12 hours and 225 parts of 4-nitrocinnamonitrile are isolated in the cold. Melting point: 202° C. The 4-nitro-cinnamonitrile thus obtained is then reduced by the Bechamp method in 2000 parts of water and 800 parts of ethyl alcohol. The 4-aminocinnamonitrile is obtained which melts at 109°–110° C. Yield: 76%.

Analysis

| Analysis | C% | H% | N% |
|---|---|---|---|
| Calculated $C_9H_8N_2$ | 75.00 | 5.55 | 19.44 |
| Found | 75.02 | 5.77 | 19.25 |

EXAMPLE 2

140 parts of m-aminocinnamonitrile are dissolved in 1000 parts of water and 220 parts by volume of 30% hydrochloric acid and are diazotised by adding 70 parts of sodium nitrite. Then a solution of 232 parts of N-cyanoethyl-N-acetyloxyethyl-m-toluidine in 200 parts of acetic acid is added and the dyestuff obtained is filtered off and dispersed. It dyes polyester fibres a yellow shade possessing excellent fastness to light and to sublimation and indeed to the conditions set out above.

The m-aminocinnamonitrile used in this Example may be prepared according to the process described in Example 1 for the preparation of p-aminocinnamonitrile, but replacing p-nitroaniline by m-nitroaniline. One obtains successively:
- the 2-chloro-3-(3-nitrophenyl) propionitrile which melts at 90° C. Yield: 60%
- the 3-nitrocinnamonitrile which melts at 160° C. Yield: 85%
- the 3-aminocinnamonitrile which melts at 84° C. Yield: 86%

Analysis

| Analysis | C% | H% | N% |
|---|---|---|---|
| Calculated for $C_9H_8N_2$ | 75.00 | 5.55 | 19.44 |
| Found | 74.68 | 5.48 | 19.44 |

EXAMPLE 3

174.5 parts of 4-amino-3-chlorocinnamonitrile are stirred for 2 hours in 220 parts of 30% hydrochloric acid and 220 parts of water. 560 parts of water are added and the mixture is diazotised with 70 parts of sodium nitrite. Then, a solution of 281 parts of N-ethyl-N-cinnamoyloxyethyl-m-toluidine in 300 parts of acetic acid is introduced gradually. The dyestuff is filtered off and dispersed. It dyes polyester fibres an orange shade possessing excellent fastness to light and to sublimation and indeed to the conditions set out above.

The 4-amino-3-chlorocinnamonitrile used in this Example may be prepared according to the process described in Example 1 for the preparation of p-aminocinnamonitrile, but replacing p-nitroaniline by 3-chloro4-nitroaniline. One obtains successively:
- the 3-(4-nitro-3-chlorophenyl)-2-chloropropionitrile which melts at 120° C. Yield: 70%
- the 3-chloro-4-nitrocinnamonitrile which melts at 106°–107° C. Yield: 72%
- the 4-amino-3-chlorocinnamonitrile which melts at 135°–136° C. Yield: 82%

Analysis

| Analysis | C% | H% | N% | Cl% |
|---|---|---|---|---|
| Calculated for $C_9H_7ClN_2$ | 60.50 | 3.92 | 15.68 | 19.89 |
| Found | 60.47 | 3.91 | 15.52 | 19.78 |

EXAMPLE 4

174.5 parts of 3-amino-4-chlorocinnamonitrile are stirred for 2 hours in 220 parts of 30% hydrochloric acid and 220 parts of water. 560 parts of water are added and the mixture is diazotised with 70 parts of sodium nitrite. Then, the solution of the diazo derivative is introduced into a solution of 238 parts of N,N-bis (2-hydroxyethyl)-N-acetyl-m-phenylenediamine in 500 parts of water. The dyestuff is isolated, dried and acetylated in 1000 parts of acetic anhydride. The greater part of the acetic anhydride is driven off and 300 parts of ethyl alcohol and 1000 parts of water are added. The dyestuff is isolated and dispersed. It dyes polyester fibres an orange yellow shade possessing excellent fastness to light and to sublimation and indeed to the conditions set out above.

The 3-amino-4-chlorocinnamonitrile used in this Example may be prepared according to the process described in Example 1 for the preparation of p-aminocinnamonitrile, but replacing p-nitroaniline by 4-chloro-3-nitroaniline. One obtains successively:
- the 3-(3-nitro-4-chlorophenyl)-2-chloropropionitrile which melts at 78°–79° C. Yield: 65%
- the 4-chloro-3-nitrocinnamonitrile which melts at 134°–135° C. Yield: 78%
- the 3-amino-4-chlorocinnamonitrile which melts at 130°–131° C. Yield: 81%

Analysis

| Analysis | C% | H% | N% | Cl% |
|---|---|---|---|---|
| Calculated for $C_9H_7ClN_2$ | 60.50 | 3.92 | 15.68 | 19.89 |
| Found | 60.31 | 3.99 | 15.47 | 19.78 |

The following Table gives other Examples of dyestuffs according to the invention of the formula:

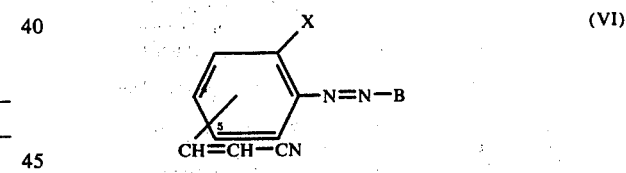

(VI)

Table I

| Example | X | Position of the radical —CH=CH—CN | Coupling compound B—H | Shade on polyester fibres |
|---|---|---|---|---|
| 5 | H | 4 | 1-phenyl-3-methyl-5-pyrazolone | yellow |
| 6 | H | 5 | " | green-yellow |
| 7 | Cl | 4 | " | yellow |
| 8 | Cl | 5 | " | green-yellow |
| 9 | H | 4 | 2'-chloro-1-phenyl-3-methyl-5-pyrazolone | yellow |
| 10 | Cl | 5 | " | green-yellow |
| 11 | H | 4 | 3'-sulphonamido-1-phenyl-3-methyl-5-pyrazolone | green-yellow |
| 12 | Cl | 4 | 1-phenyl-3-carbonamido-5-pyrazolone | orange-yellow |
| 13 | Cl | 4 | N-methyl-4-hydroxy-2-quinolone | yellow |
| 14 | H | 4 | N-ethyl-N-cyanoethyl-aniline | orange |
| 15 | H | 5 | " | orange |
| 16 | Cl | 4 | " | orange |
| 17 | Cl | 5 | " | orange |
| 18 | H | 4 | N-hydroxyethyl-N-cyanoethyl-aniline | orange |

Table I-continued

| Example | X | Position of the radical —CH=CH—CN | Coupling compound B—H | Shade on polyester fibres |
|---|---|---|---|---|
| 19 | H | 4 | N-cyanoethyl-N-acetyloxy-ethyl-aniline | orange |
| 20 | H | 5 | " | orange |
| 21 | Cl | 4 | " | orange |
| 22 | Cl | 5 | " | orange |
| 23 | H | 4 | ethyl ester of N-ethyl-N-phenyl-amino-propionic acid | orange |
| 24 | H | 4 | N,N-dimethyl-N'-acetyl-m-phenylenediamine | scarlet |
| 25 | H | 5 | " | orange |
| 26 | Cl | 4 | " | scarlet |
| 27 | H | 4 | 3'-cyano-1-phenyl-3-methyl-5-pyrazolone | green-yellow |
| 28 | Cl | 5 | N,N-dimethyl-N'-acetyl-m-phenylenediamine | orange |
| 29 | H | 4 | N-ethyl-N-acetyloxyethyl-m-toluidine | scarlet |
| 30 | H | 5 | N-methyl-N-cinnamoyloxy-ethyl-aniline | yellow |
| 31 | Cl | 4 | N-methyl-N-cinnamoyloxy-ethyl-m-toluidine | scarlet |
| 32 | Cl | 5 | N,N-di(acetyloxyethyl) aniline | orange |
| 33 | H | 4 | N,N-di(acetyloxyethyl)-N'-acetyl-m-phenylene-diamine | orange |
| 34 | H | 5 | " | orange |
| 35 | Cl | 4 | " | orange |
| 36 | Cl | 5 | " | orange |
| 37 | H | 4 | N-methyl-N-(2-carbonamido-ethyl)aniline | orange |
| 38 | H | 4 | N-ethyl-N-(2-methylsulpho-nyl-ethyl)aniline | orange |
| 39 | H | 4 | p-cresol | orange |
| 40 | H | 5 | " | yellow |
| 41 | Cl | 4 | " | orange |
| 42 | Cl | 5 | " | yellow |
| 43 | H | 4 | β-naphthol | scarlet |
| 44 | H | 4 | 3-acetylaminophenol | yellow |
| 45 | H | 5 | " | yellow |
| 46 | H | 4 | 1,1-dioxide of N-phenyl-1,4-tetrahydrothiazine | yellow |
| 47 | H | 5 | " | green-yellow |
| 48 | H | 4 | 1-N,N-di(acetyloxyethyl) amino-2-methoxy-5-acetylamino-benzene | scarlet |
| 49 | H | 4 | 3-hydroxy-diphenylene-oxide | brown-orange |
| 50 | H | 5 | 3-hydroxy-diphenylene-oxide | orange |
| 51 | Cl | 4 | 2-hydroxy-carbazole | brown-orange |
| 52 | Cl | 5 | 2-hydroxycarbazole | yellow |
| 53 | H | 4 | 7-hydroxycoumarine | yellow |
| 54 | H | 5 | " | green-yellow |
| 55 | Cl | 4 | 7-hydroxyindazole | orange |
| 56 | Cl | 5 | " | yellow |

EXAMPLE 57

140 parts of p-aminocinnamonitrile are dissolved in 1000 parts of water and 200 parts by volume of 30% hydrochloric acid and are diazotised by adding 70 parts of sodium nitrite. The solution of the diazo derivative is introduced rapidly into a solution of 123 parts of m-anisidine in 2500 parts of water and 105 parts of 30% hydrochloric acid. 2400 parts of an aqueous 20% solution of sodium acetate are added within one hour and a half, the mixture is filtered and the paste is mixed with 2500 parts of water. 400 parts of 30% hydrochloric acid are added and the amino-azo compound is diazotised with 70 parts of sodium nitrite. The solution thus obtained is introduced slowly into 232 parts of 1-phenyl-3-carbonamido-5-pyrazolone dissolved in 4000 parts of water with 40 parts of sodium hydroxide and 400 parts of calcined sodium carbonate. The dyestuff obtained, previously dispersed, dyes polyester fibres a scarlet shade possessing excellent fastness to light and to sublimation and indeed to the conditions set out above.

The following Table gives other Examples of dyestuffs according to the invention of the formula:

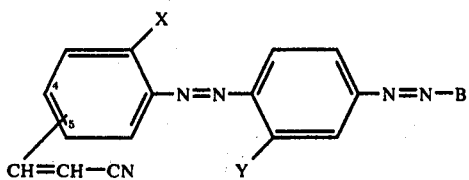

(VII)

Table II

| Example | X | Position of the radical —CH=CH—CH | Y | B | Shade |
|---|---|---|---|---|---|
| 58 | H | 4 | OCH₃ | 2-methyl-4-(n-ethyl-N-cyanoethylamino)-phenyl | bordeaux |
| 59 | H | 5 | CH₃ | 2-acetylamino-4-dimethyl-aminophenyl | violet |
| 60 | Cl | 4 | NHCOCH₃ | 1-phenyl-3-ethoxycarbonyl-5-oxopyrazol-4-yl | scarlet |
| 61 | H | 4 | CH₃ | 2-phenylindol-3-yl | scarlet |
| 62 | H | 4 | OCH₃ | 2-phenylindol-3-yl | red |

EXAMPLE 63

A fabric of ethyleneglycol polyterephthalate is printed with a printing paste which contains 20 parts of the dyestuff described in Example 4, 150 parts of the sodium salt of a sulphonated castor oil, 600 parts of a thickener and 250 parts of water. After drying, the fabric is subjected to thermal fixation for 1 minute at 200° C. and then to a reducing treatment. An orange yellow shade having good general fastness is obtained.

EXAMPLE 64

A fabric of ethylene glycol polyterephthalate is impregnated by foularding with a bath which contains 9 parts of the dyestuff obtained in Example 5, 0.5 parts of a polyglycol ether of oleyl alcohol, 1.5 parts of a polyacrylic amide and the amount of water necessary to make up to 1000 parts. After drying, the fabric is subjected to thermal fixation for 1 minute at 200° C. and then to a reducing treatment by sodium dithionite. A yellow shade is obtained.

We claim:
1. Dyestuffs of the formula:

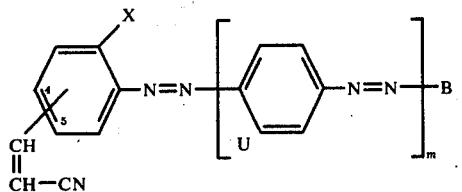

in which the radical — CH=CH—CN is fixed in the 4- or 5-position, X is hydrogen or chlorine, U is hydrogen, chlorine, alkyl containing 1 to 4 carbon atoms, alkoxy containing 1 to 4 carbon atoms, benzoylamino, cinnamoylamino, or aliphatic acylamino containing up to 2 carbon atoms, m is zero or one, and B is a. the radical of the formula:

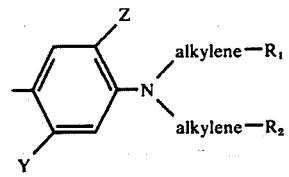

wherein Y is hydrogen, chlorine, methyl, methoxy, acetylamino, benzoylamino or cinnamoylamino, Z is hydrogen, methyl or methoxy, each alkylene bridge contains 1 to 4 carbon atoms, $R_1$ and $R_2$ are the same or different and each represent hydrogen, cyano, hydroxy, alkoxycarbonyl, acetyloxy, benzoyloxy, cinnamoyloxy, acetyl, benzoyl, cinnamoyl, alkylsulfonyl, carbonamido, or alkoxycarbonyloxy, the alkyl and alkoxy groups containing 1 to 4 carbon atoms.

b. the radical of the formula:

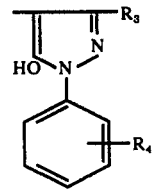

wherein $R_3$ is hydrogen, methyl, carbonamido, N-alkyl- or N,N-dialkylcarbonamido, or alkoxycarbonyl, the alkyl and alkoxy groups containing 1 to 4 carbon atoms, and $R_4$ is hydrogen, chlorine, cyano, nitro, methyl or sulphonamido, c. the p-hydroxyphenyl, 2-hydroxy-5-methylphenyl, 2-acetylamino-4-hydroxyphenyl, 2-hydroxy-1-naphthyl, or (dioxy-4,4 thiomorpholino)-4 phenyl radical, d. the 3-hydroxy-2-dibenzofuranyl or 7-hydroxy-8-coumarinyl radical, e. the 7-hydroxy-4-indazolyl radical, f. the 2-hydroxy-3-carbazolyl radical, g. the N-alkyl-4-hydroxy-2-oxo-3-quinolinyl radical, alkyl containing 1 to 4 carbon atoms or, h. the 2-phenyl-3-indolyl radical.

2. Dyestuff of the formula:

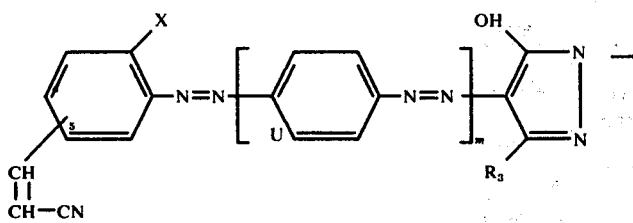

wherein the radical —CH=CH—CN is fixed in the 4- or 5-position, X is hydrogen or chlorine, $m$ is zero or one, U is hydrogen, chlorine, alkyl containing 1 to 4 carbon atoms, alkoxy containing 1 to 4 carbon atoms, benzoylamino, cinnamoylamino, or acetylamino, $R_3$ is hydrogen, methyl, carbonamido, N-alkyl- or N,N-dialkycarbonamido, or alkoxycarbonyl, the alkyl and alkoxy groups containing 1 to 4 carbon atoms, and $R_4$ is hydrogen, chlorine, cyano, nitro, methyl or sulphonamido.--

3. Dyestuff of the formula:

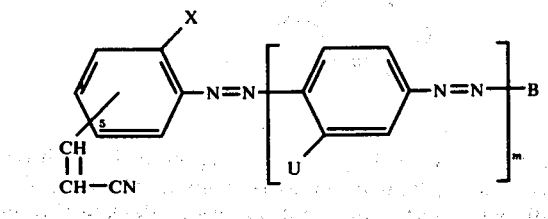

in which the radical — CH = CH-CN is fixed in the 4- or 5-position, X is hydrogen or chlorine, U is hydrogen,

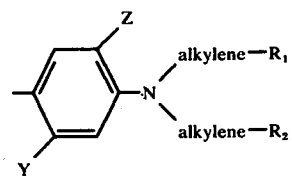

chlorine, alkyl containing 1 to 4 carbon atoms, alkoxy containing 1 to 4 carbon atoms, benzoylamino, cinnamoylamino, or aliphatic acylamino containing up to 2 carbon atoms, $m$ is zero or one, and B is a radical of the formula:

wherein Y is hydrogen, chlorine, methyl, methoxy, acetylamino, benzoylamino or cinnamoylamino, Z is hydrogen, methyl or methoxy, each alkylene bridge contains 1 to 4 carbon atoms, $R_1$ and $R_2$ are the same or different and each represent hydrogen, cinnamoyloxy, acetyl, benzoyl, cinnamoyl, alkylsulfonyl, carbonamido, or alkoxycarbonyloxy, the alkyl and alkoxy groups containing 1 to 4 carbon atoms.

* * * * *